(12) United States Patent
Kasra

(10) Patent No.: US 9,303,244 B1
(45) Date of Patent: Apr. 5, 2016

(54) HYDROSTATIC PRESSURE GENERATOR DEVICE

(71) Applicant: Mehran Kasra, Alpharetta, GA (US)

(72) Inventor: Mehran Kasra, Alpharetta, GA (US)

( * ) Notice: Subject to any disclaimer, the term of this patent is extended or adjusted under 35 U.S.C. 154(b) by 366 days.

(21) Appl. No.: 13/969,553

(22) Filed: Aug. 17, 2013

Related U.S. Application Data

(60) Provisional application No. 61/684,729, filed on Aug. 18, 2012.

(51) Int. Cl.
- *C12M 1/12* (2006.01)
- *C12M 1/34* (2006.01)
- *C12M 1/00* (2006.01)

(52) U.S. Cl.
CPC ............... *C12M 41/40* (2013.01); *C12M 29/14* (2013.01)

(58) Field of Classification Search
CPC ...... C12M 29/00; C12M 29/14; C12M 41/40; C12M 41/14
USPC ........... 435/284.1, 286.6, 288.5, 303.1, 297.2
See application file for complete search history.

(56) References Cited

U.S. PATENT DOCUMENTS

| | | | | |
|---|---|---|---|---|
| 7,422,893 B2* | 9/2008 | Diresta | ................... | C12M 23/42 435/283.1 |
| 7,603,946 B2* | 10/2009 | Zacche' | ................... | A23L 3/015 422/292 |
| 7,892,821 B2* | 2/2011 | Watanabe | .............. | C12M 23/04 422/500 |
| 2002/0009805 A1* | 1/2002 | Nevo | .................... | A61L 27/3604 435/366 |
| 2003/0133915 A1 | 7/2003 | Smith | | |
| 2004/0033482 A1* | 2/2004 | Artmann | ................... | G01L 1/00 435/4 |
| 2007/0087321 A1 | 4/2007 | Pribenszky | | |
| 2013/0111887 A1* | 5/2013 | Kwok | ..................... | F03B 17/04 60/325 |

OTHER PUBLICATIONS

Kasra et al., "Effect of Dynamic Hydrostatic Pressure on intervertebral disc cells: A rabbit model" Journal of Orthopaedic Research, 21:597-603, 2003.*
Kasra et al., "Effect of Dynamic Hydrostatic Pressure on intervertebral disc cells: A rabbit model" Journal of Orthopaedic Research, 21:597-603, 2003, USA.

* cited by examiner

*Primary Examiner* — Nina Bhat

(57) ABSTRACT

A device including a pressure generating assembly and a chamber for generating hydrostatic pressure in the said chamber. In particular, the device is useful for cell mechanical stimulation and tissue regeneration by generating hydrostatic pressure in a chamber receiving samples such as cell cultures, biological tissues, and cell seeded biomaterial constructs for the purpose of treatment with hydrostatic pressure. The pressure generating assembly of the device comprises a piston and a cylinder generating and relieving pressure by moving the piston in the cylinder using an actuating system for quick placement and removal of the piston in and out of the cylinder. The device is portable and autoclavable and can be hand operated without any tool to generate pressures at high physiological levels up to at least 10 MPa. The device has a venting system allowing vital gasses to reach the samples under treatment when the device is placed in an incubator.

27 Claims, 6 Drawing Sheets

HYDROSTATIC PRESSURE GENERATOR DEVICE

CROSS-REFERENCE TO RELATED APPLICATIONS

This application claims an invention which was disclosed in Provisional Application No. 61/684,729, filed on 18 Aug. 2012, entitled "Hydrostatic Pressure Generator Device". The benefit under 35 USC §119(e) of the U.S. provisional application is hereby claimed, and the aforementioned application is hereby incorporated herein by reference.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND

1. Field of the Invention

The invention relates to a device comprising a pressure generating assembly and a chamber for generating hydrostatic pressure in the said chamber, more particularly, a portable and autoclavable device for generating hydrostatic pressure in a fluid filled chamber receiving samples such as cell cultures, biological tissues, and cell seeded biomaterial constructs for the purpose of treatment with hydrostatic pressure.

2. Description of the Prior Art

Musculoskeletal disorders such as age-related degenerative changes of cartilage, intervertebral disc, collagen and bone contribute to some of the most common causes of impairment and disability for middle-aged and older persons, such as back pain, osteoarthritis, and degenerative joint and bone diseases. With an increasing aging population, it is therefore important to have a means for regeneration of articular cartilage, intervertebral discs as well as collagen and bone remodeling. Musculoskeletal disorders are multifactorial phenomenon and both mechanical and biological factors have been implicated in cases of accelerated degeneration.

During normal daily activities, the cartilage cells, the chondrocytes, in the cartilage of a diarthrotic joint experience levels of hydrostatic pressures in the order of 7 to 10 MPa (Hall et al., 1996) and increased cartilage thickness occurs in joint regions exposed to high intermittent hydrostatic stress (Wong et al., 1990). The intervertebral disc is routinely subjected to compressive loads that alter with posture and muscle activity and can produce pressures greater than 2 MPa in human lumbar discs in vivo (Wilke et al., 1999).

It has been shown by many studies that mechanical stimulation such as hydrostatic pressure is a major factor in maintaining load bearing tissues by influencing different biological factors at cellular level. Different studies have confirmed that hydrostatic pressure influences cellular response such a synthesis rate and increased collagen secretion by cells in major load bearing tissues such as cartilage (Smith et al., 2000) and intervertebral disc (Kasra et al. 2001, 3003, 2006).

In mechanical stimulation of intervertebral disc cells, Kasra et al. (2003) showed that within physiological levels of hydrostatic pressure up to 5 MPa, the magnitude of hydrostatic pressure was the dominant factor, and the higher the pressure the higher was the rate of protein synthesis by cells. The regenerative advantage of intermittent hydrostatic pressure at physiological levels 5-10 MPa applied to cartilage cells in vitro is also shown in U.S. Pat. Application Publication No. 20030133915A1. These studies suggest that for cell and tissue mechanical stimulation purposes related to tissue regeneration and in vitro studies of cell cultures, using hydrostatic pressures at high physiological levels of up to 10 MPa would be beneficial.

In most of research labs and commercial systems, hydrostatic pressure has usually been generated in an incubator by pressurizing the incubator gas in a vessel using a compressor. In an ordinary laboratory environment by pressurizing a gas in an incubator, it can be difficult to generate a high hydrostatic pressure, more than 1 MPa, and loading frequency is usually low and less than 1 Hz. For generating high hydrostatic pressures at high frequencies, Kasra et al. (2001) introduced a system for in vitro studies of cell cultures using a fluid filled cylindrical chamber receiving a cell culture and a piston moving in the said chamber to generate pressure, subjecting the cell culture to dynamic hydrostatic pressure. This system was operated by a servo-hydraulic external actuator and could generate pressures up to 5 MPa and 20 Hz frequencies. This method has been used in other studies such as the study reported by Le Maitre et al. (2009) related to therapy of intervertebral disc degeneration. A similar method was used in U.S. Pat. Appl. Pub. No. 20030133915A1 using a hydraulic loading instrument in fluid communication with the pressurizing chamber which could generate a dynamic hydrostatic pressure of 10 MPa at 1 Hz frequency. These fluid filled chambers operated by hydraulic systems are expensive, have a large size, not portable, and having difficulty of keeping a sanitary environment.

The concept of using a fluid filled cylindrical chamber receiving a biological tissue and a piston moving in the said chamber as reported by Kasra et al. (2001, 2003, 2005) was also used for generating very high static hydrostatic pressures up to 200 MPa for cryopreservation of cells and tissues described in U.S. Pat. Appl. Pub. No. 20070087321A1.

Ease of operation is also a major factor which has not been a priority in designing of the aforementioned hydrostatic pressure devices. For example, in U.S. Pat. Appl. Pub. No. 20070087321A1, the pressurizing chamber has two openings, one receiving a pressurizing piston and the other a pressure gauge. The pressure chamber is equipped with a cap for retaining and moving the piston inside the chamber by attaching the cap to the chamber using multiple screws. For relieving pressure in the chamber either the pressure gauge or the piston has to be removed. Removing and reinstalling the pressure gauge is not practical for multiple uses, especially if the chamber is of plastic type material, compromising the pressure gauge sealing. It is also time consuming to adjust the piston for inserting and removing the piston in and out of the chamber by screwing and unscrewing multiple screws on the cap. The system described in U.S. Pat. Appl. Pub. No. 20070087321A1 does not have any venting system and cannot be placed in an incubator and therefore not suitable for treating cell cultures in an incubator.

In most of the hydrostatic pressure devices, including the device of the U.S. Pat. Appl. Pub. No. 20070087321A1, a piston is driven directly into a pressurizing chamber containing the sample to be treated. Having the piston and the chamber of the same diameter has the disadvantage of having a limitation on the size of the chamber if the device is to be hand operated. The required load for pushing the piston in the chamber increases with the square power of the inner chamber diameter and as the inner chamber diameter increases, it increasingly becomes more difficult to operate the device by hand without any tool to generate a high hydrostatic pressure at 10 MPa level.

Sealing method is also a very important factor in the design of hydrostatic pressure devices, and it can influence the range of motion of the piston in the chamber and holding time of the pressure in the chamber as well as maintaining sealing quality after autoclaving. But there is hardly any details on sealing methods used in the disclosure of the aforementioned hydrostatic pressure devices.

Considering the advancement of the field of tissue regeneration and increasing use of hydrostatic pressure for cell and tissue mechanical stimulation, there is a need for a light, portable and easy to operate hydrostatic pressure device which can generate pressures at high physiological levels up to at least 10 MPa. This device needs to be autoclavable, quick and easy to operate by hand without any tool, and have a venting system which allows the device to be placed in an incubator without having to remove the samples from the chamber after each treatment. The ease of use and affordability of such a device is expected to provide most of laboratories with the opportunity of having an important tool for performing research in an important area of tissue regeneration and studying catabolic and anabolic responses of different cells to hydrostatic mechanical stimulation.

SUMMARY OF THE INVENTION

It is the object of the present invention to provide a device comprising a pressure generating assembly and a chamber for generating hydrostatic pressure in the said chamber. The pressure generating assembly is preferably a separate part and can be connected to the chamber. The pressure generating assembly comprises means such as a piston and a cylindrical passageway defining a cylinder, which can be placed in connection with the chamber for generating and relieving pressure in the chamber by pushing and pulling the piston in the cylinder. The terms pressure and hydrostatic pressure are used interchangeably.

The chamber and the cylinder can be filled with a fluid and a gas, generating higher pressure with more fluid volume and having the maximum pressure when the chamber and the cylinder are fully filled with a fluid.

The systems, devices and methods of the invention are particularly suited for use in treatment of cell cultures, biological tissues, and cell seeded biomaterial constructs in a sterile condition for the purpose of treatment with the hydrostatic pressure preferably at physiological levels up to at least 10 MPa.

The system and method of the invention provide many advantages and new features including the following:

(1) The device is light and portable.
(2) Depending on its size, the device can be operated by hand without any tool generating hydrostatic pressures up to at least 10 MPa, or it can be operated by hand using a tool such as a wrench. The device can also be operated using an external actuator for applying hydrostatic pressures within a wide range of amplitudes and frequencies.
(3) The device is autoclavable and can be used in a sterile condition.
(4) The device comprises a venting system allowing the vital gases to reach the device chamber when placed in an incubator.
(5) The pressure generating assembly of the device comprises self adjusting means for quick placement and removal of its piston in and out of its cylinder for generating and relieving pressure in the device chamber, making the use of the device very quick and easy.
(6) Having the device with its pressure generating assembly as a separate part from its chamber, the piston and cylinder of the pressure generating assembly can have a smaller cross-sectional area than that of the chamber cavity where the pressure is generated. Having a a smaller piston cross-sectional area than that of the chamber cavity, the device can generate pressures with much less effort compared to a device with equal piston and chamber cavity cross-sectional areas.

In a preferred embodiment, the device comprising:

(a) A pressure generating assembly comprising a main body, an actuating body, a piston and its sealing member such as an oring, a central stud, and a shield.

The main body comprises a cavity at its top and a cylindrical passageway, namely cylinder, at its lower part extending between the main body top cavity and the exterior. There are a plurality of openings in the wall of the main body extending between the main body top cavity and exterior for venting purposes.

The actuating body comprises an internal passageway for receiving the piston and the central stud. The central stud can be threadebly mounted in the passageway of the actuating body and used for restraining the head of the piston in the passageway. The actuating body moves threadebly inside the main body pushing and pulling the piston in the cylinder of the main body for generating pressure.

The shield is placed on the main body in front of the venting openings of the main body to prevent the direct flow of air or gas into the device and reduce the chance of contamination.

(b) A chamber comprising of a cavity (chamber cavity) wherein a sample is received and pressure is generated and an opening (chamber opening) connecting the chamber cavity to the exterior of the chamber. The main body of the pressure generating assembly can be threadebly mounted and sealed to the chamber opening using a sealing member. After mounting the main body of the pressure generating assembly at the chamber opening, the cylinder of the main body will be in connection with the chamber cavity and by moving the piston in the cylinder, pressure is generated in the chamber cavity. The chamber cavity comprises another opening for receiving a pressure gauge and its sealing member for monitoring the generated pressure. The seal type of connections of the pressure generating assembly and the pressure gauge to the chamber is preferably a face seal comprising preferably of an oring as the sealing member placed in a gland preferably in a shape of a half groove.

In another embodiment of the present invention, there is no cylinder in the main body and the piston moves directly in the chamber cavity to generate pressure.

Still in another embodiment of the present invention, when a hydrostatic pressure generator device is mainly operated by an external actuator, there is no central stud and the piston passes through and outside the internal passageway of the actuating body for actuation thereof by an external actuator, and a breading passageway connects the main body top cavity to the cylinder of the main body allowing passage of air or gas into chamber during dynamic movement of the piston.

Still yet in another embodiment of the present invention, a hydrostatic pressure generator device is used for generating negative pressure, lower than atmospheric pressure, by suction, and the main body comprises a bleeding passageway connecting the chamber cavity to the outside of the chamber allowing passage of air or a gas out of the chamber cavity when pushing the piston in the cylinder of the main body, and after closing and sealing the passageway with a nut and a sealing member, the suction is generated by pulling the piston out of the cylinder.

Still yet in another embodiment of the present invention, the main body is mounted and fixed in the chamber opening using a plurality of screws, and the central stud is mounted and fixed in the internal passageway of the actuating body using a pin.

In the described embodiments of the present invention, the hydrostatic pressure generator device may be used without any pressure gauge and instead the pressure can be calculated by measuring the applied load or torque on the actuating body using a formula relating the applied load or torque to the pressure.

BRIEF DESCRIPTION OF THE DRAWINGS

A fuller understanding of the nature and objects of the present invention will become apparent upon consideration of the following detailed description taken in connection with the accompanying drawings, wherein.

DETAILED DESCRIPTION OF THE PREFERRED EMBODIMENTS

The invention will now be described in detail with reference to the accompanying drawings.

Figure 1:
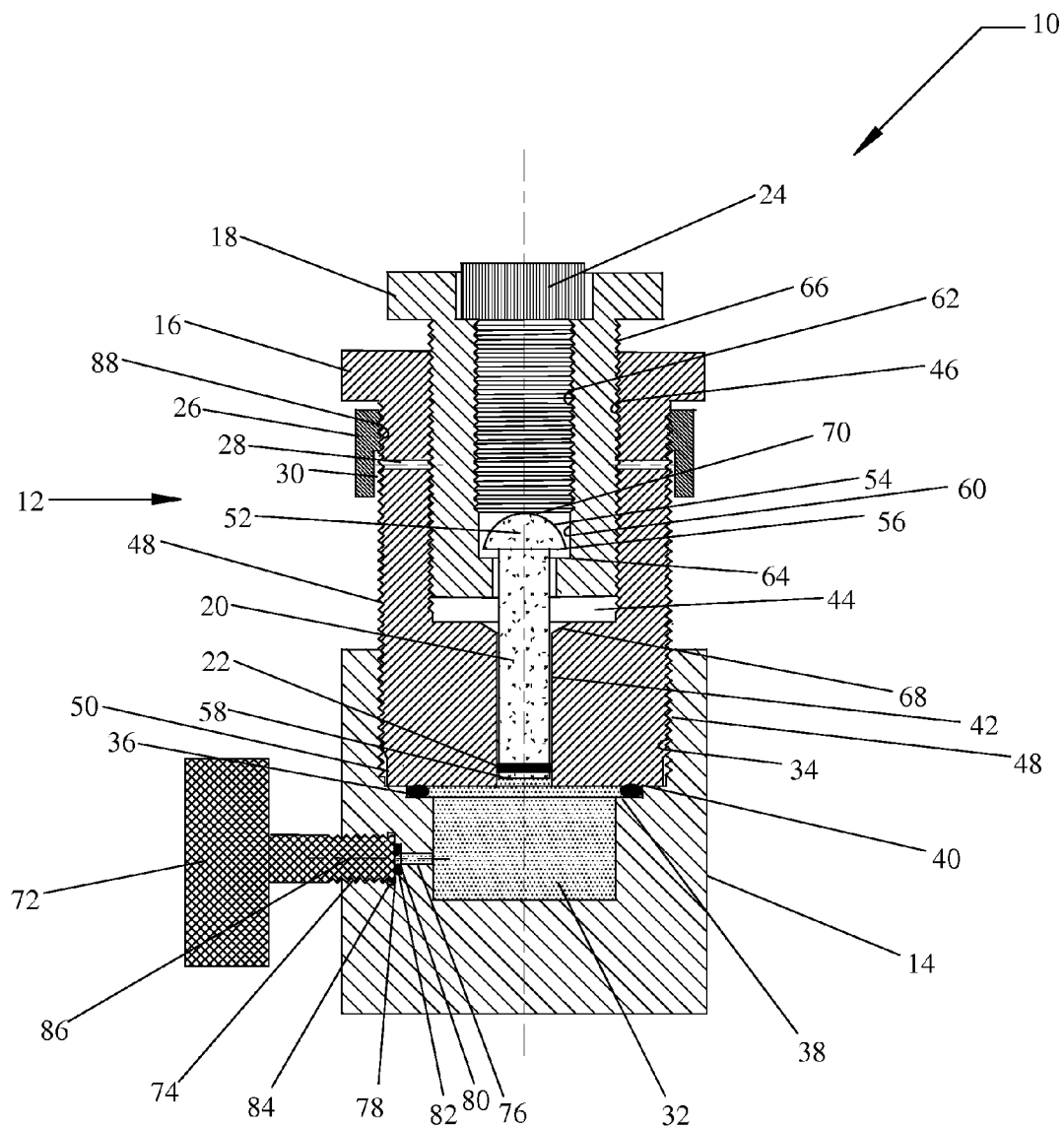
FIG. 1 is a cross-section view of a preferable embodiment of the hydrostatic pressure generator device in pressurizing position.
Figure 2:
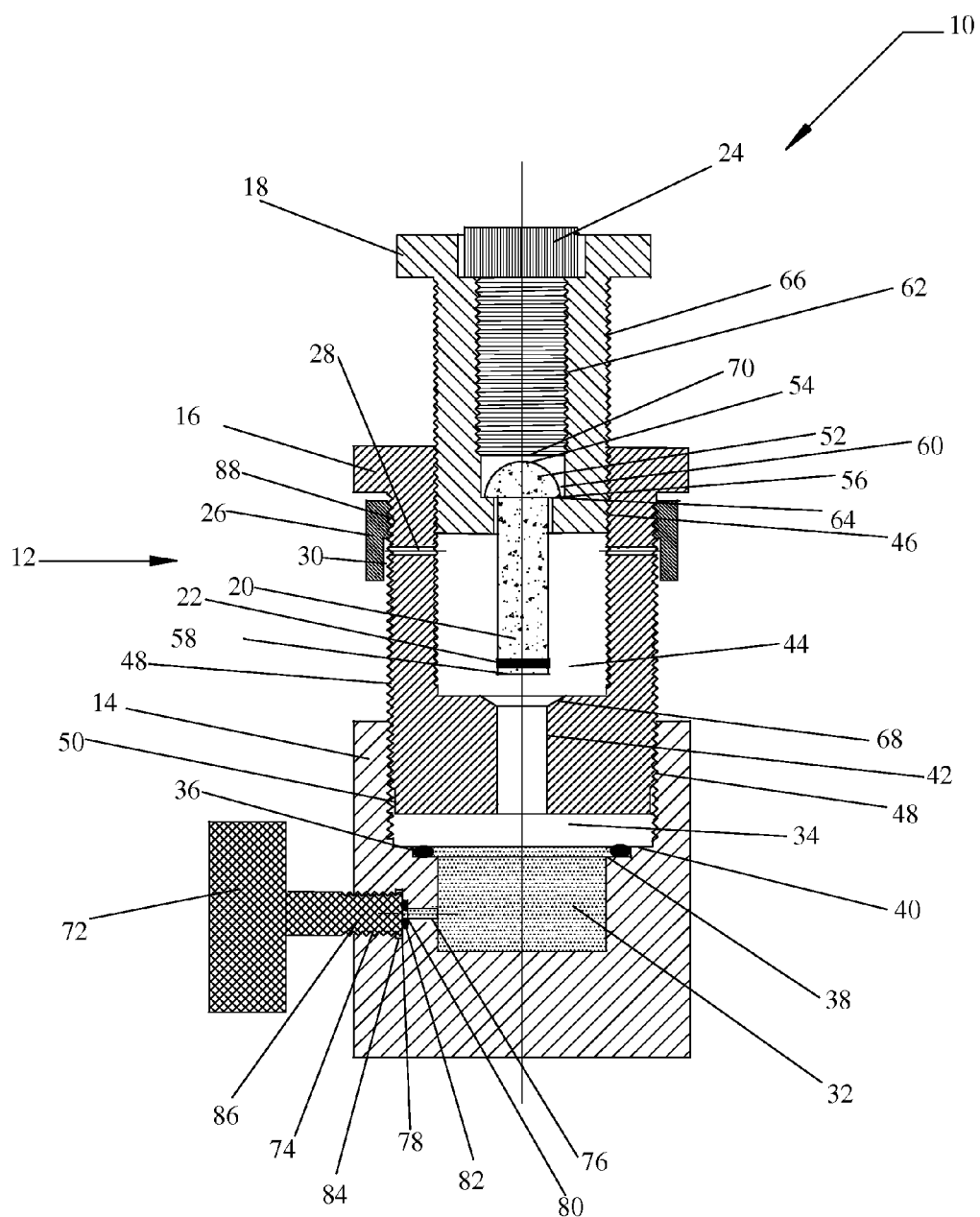
FIG. 2 is a cross-section view of the same embodiment of the hydrostatic pressure generator device shown in FIG. 1 in venting position.

FIGS. 1 and 2, show a hydrostatic pressure generator device 10 according to an embodiment of the present invention. As hereinafter described, the hydrostatic pressure generator device 10 is operated between a pressurizing position and a retracting or venting position. The pressurizing position is shown in FIG. 1 and the venting position is shown in FIG. 2.

In accordance with a preferred embodiment illustrated in FIGS. 1 and 2, hereinafter referred to as the first embodiment, the hydrostatic pressure generator device 10 comprises a pressure generating assembly 12 and a chamber 14. The pressure generating assembly 12 comprises a main body 16, an actuating body 18, a piston 20 and its sealing member 22 such as an oring, a central stud 24 such as a bolt, and a shield 26 in front of a plurality of venting openings 28 in the wall of the main body 16 with a gap 30 preferably of about 1-2 mm.

The chamber 14 comprises of a chamber cavity 32 and a chamber opening 34 located at the bottom and top parts of the chamber 14 respectively. The chamber cavity 32 receiving materials to be exposed to hydrostatic pressure including a sample, a fluid, and air, having a higher maximum pressure with a higher fluid to air volume ratio. Preferably, the sample placed in the chamber cavity 32 can be a biological tissue or a cell culture dish and the liquid can be a cell culture media. The chamber opening 34 has a threaded wall and is where the main body 16 of the pressure generating assembly 12 is mounted and sealed to the chamber 14 using a sealing member 36, such as an oring, that sits in a half grove on a step 38 above the chamber cavity 32. A step 40 above the step 38 makes the sealing surface for a face seal between the main body 16 of the pressure generating assembly 12 and the chamber 14.

Main body 16 comprises a cylindrical passageway defining a cylinder 42 at its lower part and a cavity 44 (main body cavity) with an opening on top. The cylinder 42 extends between the main body cavity 44 and the exterior of the main body 16. The main body 16 is threaded internally on the wall 46 of the main body cavity 44 as well as externally on its outer surface 48.

The pressure generating assembly 12 can be threadebly mounted and sealed to the chamber 14 by turning the main body 16 into the chamber opening 34. There is preferably a smooth surface 50 with a reduced section at the lower end of the main body 16 that allows the full travel of the main body 16 into the chamber opening 34 until it pushes against the step 40 and the sealing member 36 making a sealed connection.

At its upper end, the piston 20 has a flange 52, with a head 54, preferably rounded, and a step 56. The flange 52 is loosely secured in the actuating body 18 for actuation thereof, and the lower end 58 of the piston 20 moves in the cylinder 42 of the main body 16 to generate pressure.

Through the actuating body 18 there is an internal passageway 60 which is threaded on its upper part 62 and having a step 64 at its lower end above which the piston flange 52 is fitted for actuation thereof. The actuating body 18 is threaded on its outer surface 66 and moves threadably inside the cavity 44 of the main body 16.

The actuating body 18 provides an actuating means for holding and moving the piston 20. The piston 20 can move down and up in the cylinder 42 of the main body 16 by screwing and unscrewing rotation of the actuating body 18 in and out of the main body 16, which pushes and pulls the piston 20 in the cylinder 42. There is a taper 68 at the top of the cylinder 42 to provide a smooth entry of the piston 20 into the cylinder 42.

The central stud 24 can be screwed in the threaded portion 62 of the internal passageway 60 of the actuating body 18. The lower wall 70 of the central stud 24 can touch the head 54 of the flange 52 of the piston 20 by screwing the actuating body 18 into the main body 16 pushing the piston 20 into the cylinder 42 of the main body 16 generating pressure in the chamber cavity 32.

Self adjusting means for entering the piston 20 inside the cylinder 42 is provided by having the flange 52, with the rounded head 54, loosely secured above the step 64 in the actuating body 18, and having the taper 68 at the top of the cylinder 42, which allows a smooth entry of the piston 20 into the cylinder 42, prevents jamming of the piston 20 inside the cylinder 42, and improves sealing performance of the sealing member 22 between the piston 20 and the cylinder 42.

The amount of pressure generated in the chamber cavity 32 can be monitored by using a pressure monitoring device 72, preferably an autoclavable or a sanitary pressure gauge. The term pressure gauge represents any pressure monitoring device such as a mechanical pressure gauge as well as different types of pressure transducers, pressure sensors, and pressure transmitters.

The pressure gauge 72 is connected to the chamber 14 via a passageway including two sections of an outer hole 74 and an inner hole 76. The outer hole 74 is threaded receiving the pressure gauge 72, and the inner hole 76 connects the outer hole 74 to the chamber cavity 32.

There are two steps 78 and 80 between the outer hole 74 and inner hole 76 providing a sealing surface and a half groove gland respectively for a sealing member 82 such as an oring. The pressure gauge 72 can be threadably mounted in the outer hole 74. There is preferably a clearance groove or undercut 84 at the end of threaded portion of the outer hole 74 before the step 78 allowing the full travel of the stud 86 of the pressure gauge 72 to the end of the outer hole 74 pushing against the step 78 and sealing member 82 making a face seal between the pressure gauge 72 and the chamber 14.

As shown in FIG. 2, by unscrewing the actuating body 18 out of the main body 16, the wall of the step 64 of actuating body 18 can touch the wall of the step 56 of the piston 20, pulling the piston 20 out of the cylinder 42 of the main body 16 relieving pressure in the chamber cavity 32.

The actuating body 18 can be unscrewed and moved upward in the main body 16 until it uncovers the venting openings 28 from inside of the main body 16 in the cavity 44. With the venting openings 28 uncovered and the piston 20 out of the cylinder 42, the vital gases required for survival of cells or biological tissues placed in the chamber cavity 32 can then be provided when the assembly is placed in an incubator. To reduce the chance of contamination, the shield 26 is placed in front of the venting openings 28 with a gap 30 preferably of about 1-2 mm. The shield 26 can be threaded on its inner surface 88 and installed threadably on the main body 16 in front of the venting openings 28. In an alternative method, instead of the shield 26, filters may be installed in the venting openings 28.

In operation, referring to FIG. 1, a sample to be treated with the hydrostatic pressure is placed in the chamber cavity 32, then the main body 16 is mounted and sealed in the chamber opening 34. Then, from the top opening of the cylinder 42 in the main body 16, the chamber cavity 32 and the cylinder 42 can be filled with a fluid, such as a cell culture media. Finally, the actuating body 18 is mounted in the cavity 44 of the main body 16 and hydrostatic pressure is generated in the chamber cavity 32 by rotating and screwing the actuating body 18 in the main body 16 as described. The chamber cavity 32 and the cylinder 42 can be filled with fluid and air, generating higher pressure with more fluid volume and having the maximum pressure when the chamber cavity 32 and the cylinder 42 are fully filled with liquid.

Depending on the size of the piston 20, hydrostatic pressure magnitude, and static or dynamic choice of hydrostatic pressure, rotating action for screwing and unscrewing of the actuating body 18 into and out of the main body 16 can be done by hand without any tool, by hand with a tool such as a wrench, or by using a coupling mechanism to a rotary actuator. For turning and holding purposes, handles may be installed on the actuating body 18, the main body 16, and the chamber 14.

A prototype of the first embodiment shown in FIGS. 1 and 2 was made and tested successfully in all of its operating procedure as described. Using the prototype with a piston of 8 mm, pressures up to 10 MPa could easily be generated by rotating the actuating body 18 simply by hand and without any tools.

In a hydrostatic pressure generator device, such as the hydrostatic pressure generator device 10, other sealing systems for sealing of the pressure gauge 72 and the main body 16 to the chamber 14 may be used. For example, a gasket or an oring with different gland types can be used to seal the main body 16 or the pressure gauge 72 to the chamber 14, or a Teflon tape can be used to seal the pressure gauge 72 to the chamber 14. However, the sealing system shown in FIGS. 1 and 2 is preferable.

Preferably, the chamber 14, the chamber cavity 32, the chamber opening 34, the actuating body 18, and the main body 16 have cylindrical shapes as shown in FIGS. 1 and 2. The size of the hydrostatic pressure generator device can vary according to the size of its chamber cavity 32 which may be a miniature chamber to hold a small piece of a tissue, a small chamber to hold one culture dish, or a large chamber to hold a cell culture plate. The preferable sizes for the chamber cavity 32 are those which can receive a small commercially available single culture dish such as a 35 mm diameter cell culture dish or single cell culture dish inserts of diameters equal or less than 30 mm, plus 2-5 mm extra space around and on top of a dish for handling. The dishes can also be placed in the chamber cavity 32 in a stack and the height of the chamber cavity 32 can be adjusted according to the number of dishes in the stack.

The construction details of the invention, such as the hydrostatic pressure generator device 10 shown in FIGS. 1 and 2, are that the hydrostatic pressure generator device 10 preferably is made from materials which are autoclavable, resistant to corrosion, and do not cause any destructive reaction with the cell culture media. The preferable materials are polycarbonate, polyamide, Teflon, and stainless steel. The materials should also be sufficiently rigid and strong to hold a hydrostatic pressure of interest according to the size of the hydrostatic pressure generator device 10. Stainless steel is preferable for miniature sizes which strength is of prime importance. Polyamide and Teflon may be used for large sizes when having a low weight becomes important. More preferably polycarbonate and still more preferably a combination of polycarbonate and stainless steel may be used for having an optimum strength and size with a low weight.

Figure 3:
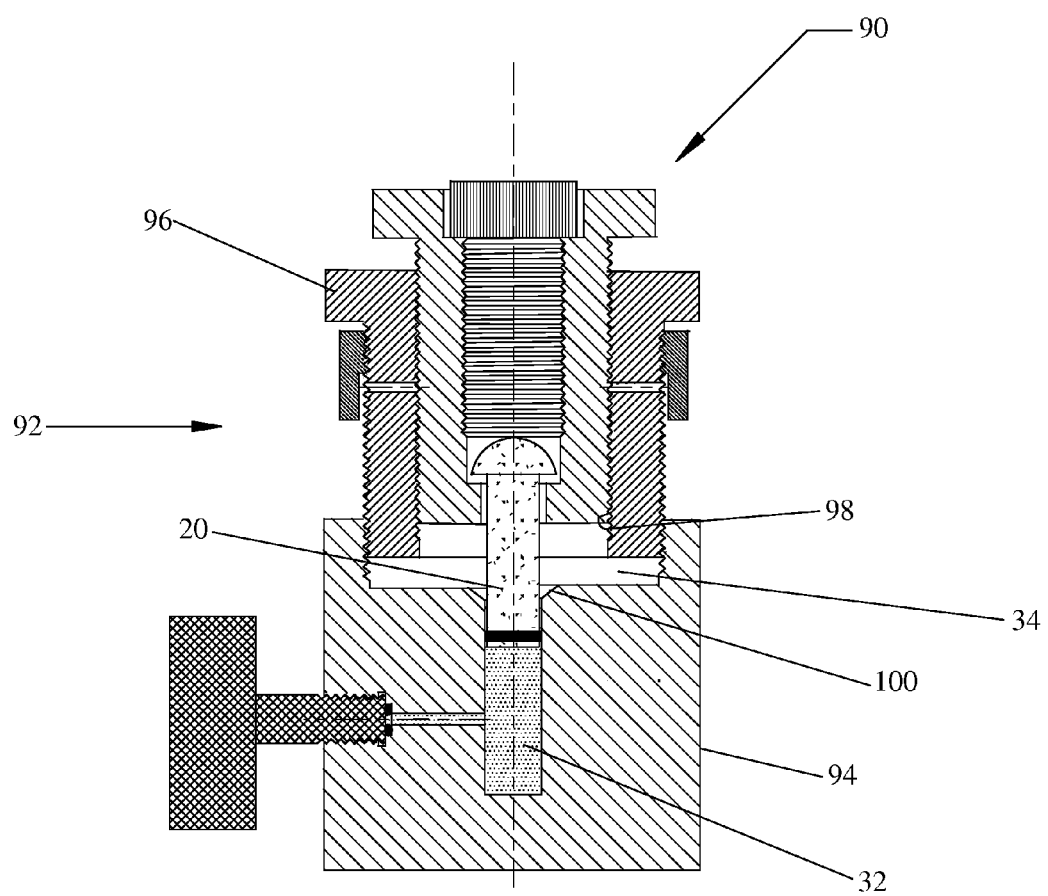
FIG. 3 is a cross-section view of another embodiment of the hydrostatic pressure generator device wherein the piston moves directly in the chamber cavity.

Reference will now be made to FIG. 3 which shows another embodiment of the present invention, generally denoted by the reference 90, comprising a pressure generating assembly 92 and a chamber 94. In FIG. 3, for simplicity and brevity, like components are given the same reference numeral as in the first embodiment shown in FIGS. 1 and 2, and the description is not repeated. In the embodiment of FIG. 3, the chamber 94 and a main body 96 respectively replace the chamber 14 and main body 16 of the first embodiment shown in FIGS. 1 and 2.

In the embodiment of FIG. 3, the main body 96 includes a threaded passageway 98 (main body passageway) without any cylinder at its lower part, and the piston 20 moves directly in the chamber cavity 32 to generate pressure. There is a taper 100 at the top of the chamber cavity 32 to provide a smooth entry of the piston 20 into the chamber cavity 32. The pressure generating assembly 92 can be mounted to the chamber 94 by screwing the main body 96 into the chamber opening 34 without using any sealing. In this embodiment, the main body 96 can be a separate part and to be connected to the chamber 94 as described and shown in FIG. 3, or the main body 96 can be integral with the chamber 14 wherein the main body 96 is an extension of the chamber opening 34. For generating pressures up to 10 MPa by hand without any tools, this embodiment is preferable for a small hydrostatic pressure generator device with a cylindrical chamber cavity 32 of a diameter of less than 10 mm and more preferably less than 8 mm.

Figure 4:
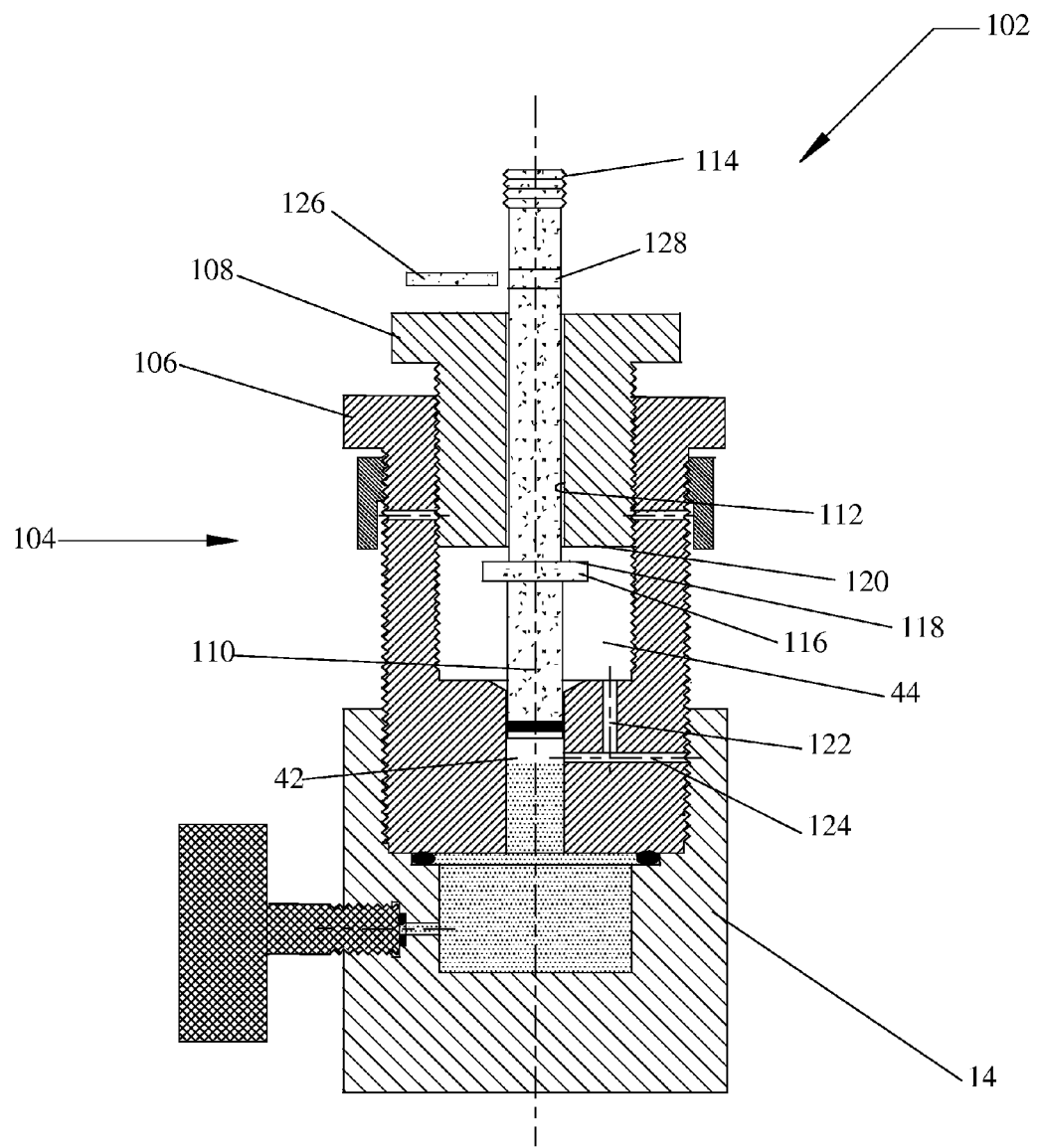
FIG. 4 is a cross-section view of another embodiment of the hydrostatic pressure generator device which is mainly used to operate with an external actuator.

Reference will now be made to FIG. 4 which shows another embodiment of the present invention, when a hydrostatic pressure generator device, generally denoted by the reference 102, is mainly operated by an external actuator. The hydrostatic pressure generator device 102 comprises a pressure generating assembly 104 and the chamber 14. In FIG. 4, for simplicity and brevity, like components are given the same reference numeral as in the first embodiment shown in FIGS. 1 and 2, and the description is not repeated. In the embodiment of FIG. 4, a main body 106, an actuating body 108, and a piston 110 respectively replace the main body 16, the actuating body 18, and the piston 20 of the first embodiment shown in FIGS. 1 and 2.

In more detail, still referring to the invention of FIG. 4, the actuating body 108 comprises a central passageway 112 with a smooth surface throughout its length wherein the piston 110 passes through and outside the actuating body 108. The piston 110 comprises a head 114 which can be engaged with an external actuator. There is a flange 116 on the piston 110 with an upper surface 118 which is located under the lower surface 120 of the actuating body 108. By screwing the actuating body 108 into the main body 106, the lower surface 120 of actuating body 108 touches the upper surface 118 of the piston flange 116 pushing the piston 110 in the cylinder 42 of the main body 106 generating a hydrostatic pressure as a baseline static hydrostatic pressure preload. From the baseline pressure, using an external actuator, applying a static or dynamic load at the piston head 114 can then generate a static or dynamic hydrostatic pressure.

In further detail, still referring to the invention of FIG. 4, there is a passageway, which maybe in a form of a vertical hole 122 connected to a horizontal hole 124, connecting the cavity 44 of the main body 106 to the inside of the cylinder 42 at its upper end allowing passage of air or incubator gas for breathing during dynamic movement of the piston 110. This embodiment can also work independent of an external actuator for generating hydrostatic pressure as described for generating a static hydrostatic pressure preload. Unloading of the hydrostatic pressure can be done by means pulling the piston 110 out of the cylinder 42 such as by unscrewing the actuating body 108 out of the main body 106 until it pushes against a pin 126 which can be fit in a hole 128 at the top of the piston 110 and pulling the piston 110 out of the cylinder 42 of the main body 106.

Figure 5:
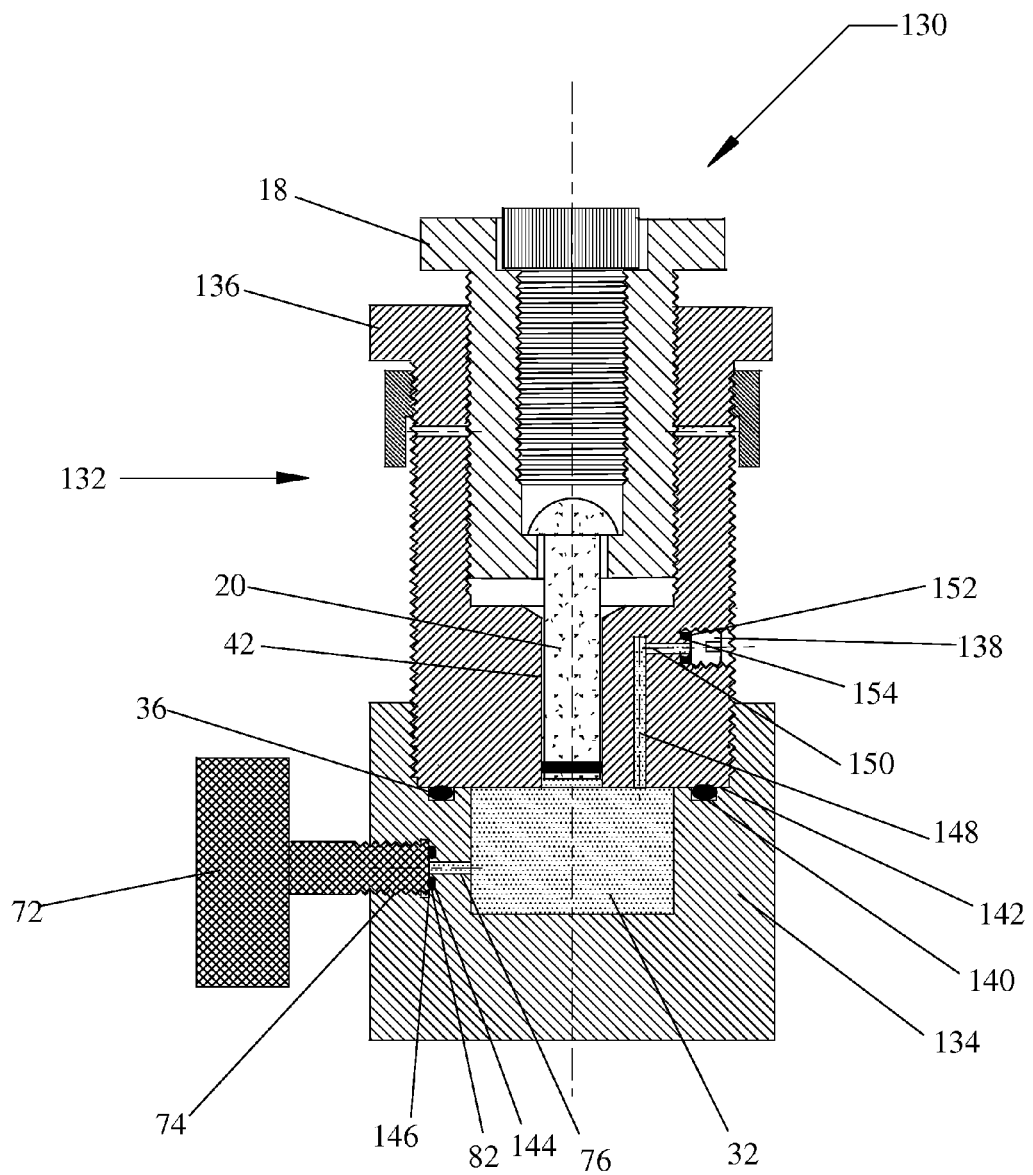
FIG. 5 is a cross-section view of another embodiment of the hydrostatic pressure generator device for generating negative pressure, lower than atmospheric pressure, by suction.

Reference will now be made to FIG. 5 which shows another embodiment of the present invention, when a hydrostatic pressure generator device generally denoted by the reference 130, is used for generating negative pressure, lower than atmospheric pressure, by suction. The hydrostatic pressure generator device 130 comprises a pressure generating assembly 132 and a chamber 134. In FIG. 5, for simplicity and brevity, like components are given the same reference numeral as in the first embodiment shown in FIGS. 1 and 2, and the description is not repeated. In the embodiment of FIG. 5, a main body 136 and the chamber 134 respectively replace the main body 16 and the chamber 14 of the first embodiment shown in FIGS. 1 and 2, and a nut 138 with its sealing assembly is added.

In more detail, still referring to the invention of FIG. 5, the sealing systems of the main body 136 and the pressure gauge 72 to the chamber 134 are preferably face seals with groove glands suitable for a negative pressure in the chamber cavity 32. The sealing of the main body 136 to the chamber 134 includes the sealing member 36, such as an oring, fitted in a groove 140 in the step 142 at the top of the chamber cavity 32. The sealing of the pressure gauge 72 to the chamber 134 includes the sealing member 82, such as an oring, fitted in the groove 144 in a step 146 between the outer hole 76 and the inner hole 74. In the main body 136, there is a bleeding passageway which may consist of a vertical section 148 and a horizontal section 150 connecting the chamber cavity 32 to the outside of the chamber 134 through the lower part of main body 136. The horizontal section 150 can be sealed with a face seal assembly consisting of the nut 138 and a sealing member 152 such as an oring, sitting in a groove 154.

In the embodiment of FIG. 5, the negative pressure in the chamber cavity 32 can be generated by removing the nut 138 from the horizontal section 150, then screwing the actuating body 18 into the main body 136 pushing the piston 20 into the cylinder 42 of the main body 136 until the fluid in the chamber rises up to the horizontal section 150, then screwing back the nut 138 in the horizontal section 150 and seal the passage, and finally generating negative pressure by unscrewing the actuating body 18 out of the main body 136 and pulling the piston 20 out of the cylinder 42.

Figure 6:
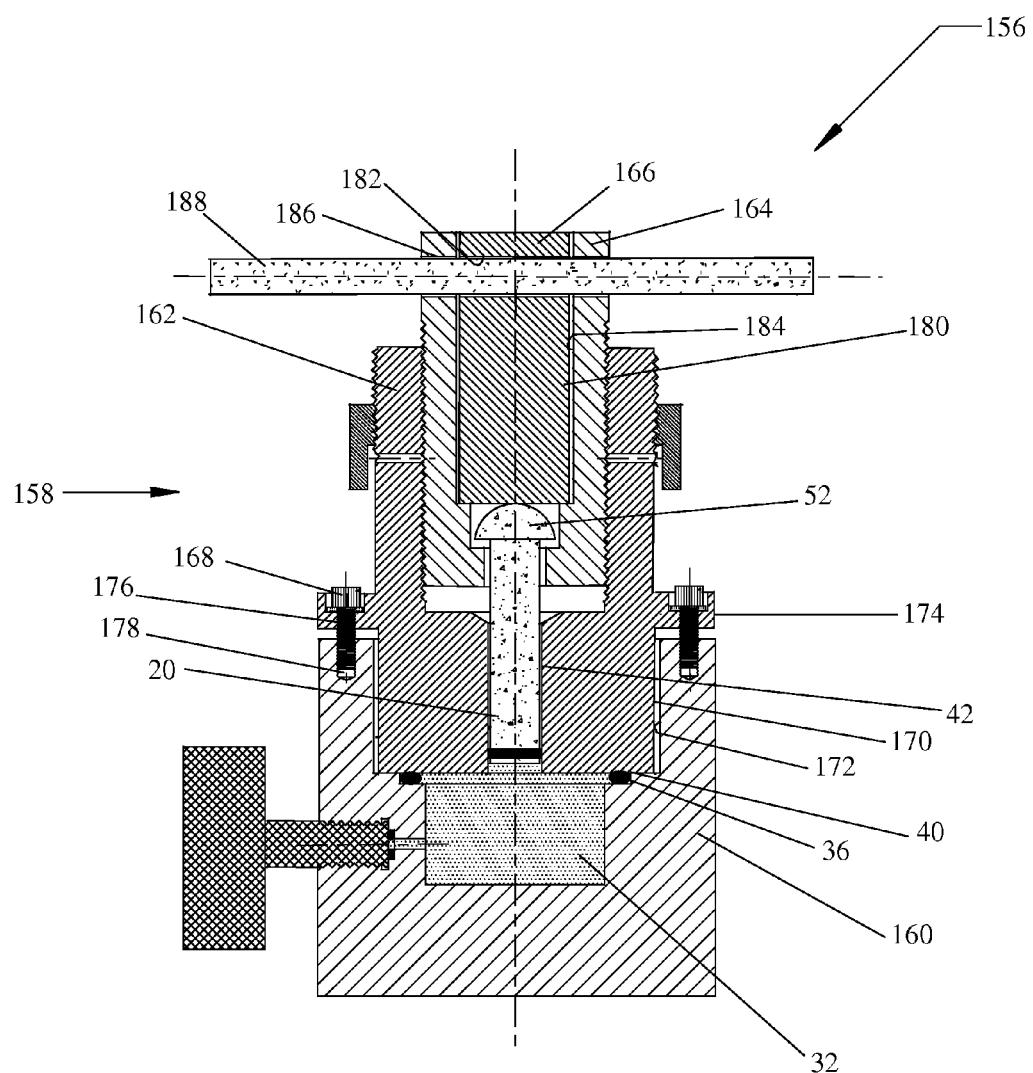
FIG. 6 is a cross-section view of another embodiment of the hydrostatic pressure generator device showing alternative methods for mounting the main body of the pressure generating assembly to the chamber using a plurality of screws, and the central stud in the actuating body using a pin.

Reference will now be made to FIG. 6 which shows another embodiment of the present invention generally denoted by the reference 156 comprising a pressure generating assembly 158 and a chamber 160. In FIG. 6, for simplicity and brevity, like components are given the same reference numeral as in the first embodiment shown in FIGS. 1 and 2, and the description is not repeated. In the embodiment of FIG. 6, the chamber 160, a main body 162, an actuating body 164, and a central stud 166 respectively replace the chamber 14, main body 16, the actuating body 18, and the central stud 24 of the first embodiment shown in FIGS. 1 and 2.

In FIG. 6 an alternative connecting means to that of the first embodiment shown in FIGS. 1 and 2, for connecting the main body 162 to the chamber 160 is shown, which uses a plurality of screws 168 to attach the main body 162 to the chamber 160. The main body 162 comprises a lower part 170 with a smooth surface which fits in the chamber opening 172 which also have a smooth surface. There is a flange 174 on the main body 162 with a plurality of openings 176 where the screws 168 can pass. On the top edge surface of the chamber 160, there are plurality of threaded holes 178 matching the treads of screws 168. The screws 168 can pass through the openings 176 of the flange 174 and be screwed in the threaded holes 178 in the chamber 160 connecting the main body 162 into chamber 160 pushing the lower surface of the main body 162 against the step 40 and the sealing member 36 sealing the connection.

Still referring to FIG. 6, in case of using a material such as Teflon which may not be strong enough for the threaded holes 178 to hold the screws 168, the holes 178 in the chamber 160 may be extended as a passageway to the of the chamber 160 where the screws 168 with a long stem can pass and be fixed with a bolt at the bottom from outside of the chamber 160. The main body 162 is preferably used with the chamber cavity 32 of a diameter preferably larger than 40 mm. The main body 164 can also be used with the actuating body 18 and the central stud 24 of the first embodiment shown in FIGS. 1 and 2.

In the embodiment of FIG. 6, the central stud 166 has the same function as the central stud 24 of the first embodiment, shown in FIGS. 1 and 2, in restraining the flange 52 of the piston 20. The central stud 166 comprises a smooth surface 180 and a hole 182 across its upper end. The actuating body 164 also comprises a smooth passageway 184 with a hole 186 at its upper end. The central stud 166 can fit in the passageway 184 and fixed with a pin 188 which passes through the holes 182 and 186. The pin 188 can also be used as a handle for rotating the actuating body 164 pushing the piston 20 in the cylinder 42 of the main body 162 generating pressure.

Referring to FIG. 6, the actuating body 164 operated with the pin 188 as a handle is preferably used with the piston 20 of a diameter of less than 8 mm so that it could be rotated by hand to generate a hydrostatic pressure of at least up to 10 MPa.

The actuating body 164 with the stud 166, shown in FIG. 6, can also be used with the main body 16 and the chamber 14 of the first embodiment, shown in FIGS. 1 and 2.

In the embodiment of FIG. 6, the cross sectional area of the chamber cavity 32 can have any shape which preferably matches the shape of the main body 162 cross sectional area. For example, both the chamber cavity 32 and the main body 162 preferably have the same shape of either circular or rectangular sections, but a circular section with a cylindrical chamber is preferable.

In the described embodiments, a hydrostatic pressure generator device, such as the hydrostatic pressure generator device 10 shown in FIGS. 1 and 2 may also be used without any pressure gauge 72 and instead the pressure can be calculated by measuring the applied torque on the actuating body 18 using a formula relating the applied torque to the pressure. Similarly, a hydrostatic pressure generator device, such as the hydrostatic pressure generator device 102 shown in FIG. 4, may also be used without any pressure gauge 72 and instead the pressure can be calculated by measuring the axial load on the piston 110 using a formula relating the axial load to the pressure.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

REFERENCES

US Patent Documents
20030133915 A1 7/2003 Smith et al.
20070087321 A1 4/2007 Pribenszky and Molnar
Other Publications
Kasra et al., Abstract of a publication entitled "Effect of dynamic hydrostatic loading on rabbit disc cells", American Society of Mechanical Engineers, Bioengineering Division (Publication) BED, 50:191-192, 2001.
Kasra et al., "Effect of Dynamic Hydrostatic Pressure on intervertebral disc cells: A rabbit model" Journal of Orthopaedic Research, 21:597-603, 2003.
Kasra et al., "Frequency response of pig intervertebral disc cells subjected to dynamic hydrostatic pressure", Journal of Orthopaedic Research., 24(10):1967-1973, 2006.
Smith et al., "Time-dependent effects of intermittent hydrostatic pressure on articular chondrocyte type II collagen and aggrecan mRNA expression" Journal of Rehabilitation Research and Development, 37:153-161, 2000.
Hall et al., "The cellular physiology of articular cartilage", J. Exp. Physiol, 81:535-545, 1996.
Wong M, Carter D R. Theoretical stress analysis of organ culture osteogenesis. Bone, 11:127-31, 1990
Wilke et al., "New in vivo measurements of pressures in the intervertebral disc in daily life" Spine, 24:755-762, 1999.
Le Maitre et al., "Development of an in vitro model to test the efficacy of novel therapies for IVD degeneration" J Tissue Eng Regen Med. 3:461-469, 2009.

I claim:
1. A device for generating hydrostatic pressure, the device comprising:
(a) a chamber comprising a chamber cavity wherein hydrostatic pressure is generated;
(b) a pressure generating assembly configured to connect to the chamber for generating hydrostatic pressure in the chamber cavity, the pressure generating assembly comprising:
(i) a main body, which includes a main body cavity and a cylindrical passageway, the cylindrical passageway defining a cylinder, wherein the cylinder extends between the main body cavity and the exterior of the main body;
(ii) a piston moving inside the cylinder of the main body to generate hydrostatic pressure;
(iii) piston sealing means for providing a seal around the piston and with the interior walls of the cylinder;
(iv) an actuating body threadably moving in the cavity of the main body;
(v) the actuating body comprising means to hold and move the piston;
(vi) self adjusting means to adjust the piston position for entering inside the cylinder;
(c) connecting means to connect the pressure generating assembly to the chamber; and
(d) first chamber sealing means for providing a seal between the pressure generating assembly and the chamber.
2. A device as claimed in claim 1, wherein the chamber cavity holding materials comprising a fluid medium and wherein the cylinder being in fluid communication with the chamber cavity.
3. A device as claimed in claim 1, wherein the connecting means is configured to connect the main body of the pressure generating assembly to the chamber by a threading mechanism, a plurality of fastening bolts and nuts, or draw latches.
4. A device as claimed in claim 1, wherein the first chamber sealing means defines a first face seal, which includes a first half groove gland in the chamber at the sealing surface between the chamber and the main body of the pressure generating assembly and a first sealing member placed in the first half groove gland.
5. A device as claimed in claim 1, the device further comprises a pressure monitoring device wherein the chamber is configured to connect to the pressure monitoring device, and second chamber sealing means for providing a seal between the pressure monitoring device and the chamber.
6. A device as claimed in claim 5, wherein the chamber comprises a passageway extending between the chamber cavity to the exterior of the chamber, the passageway includes an outer hole and an inner hole being interconnected, the inner hole has a smaller cross-sectional area than that of the other hole, the inner hole connects the outer hole to the chamber cavity, and the pressure monitoring device threadably mounted in the outer hole, and wherein the second chamber sealing means defines a second face seal, which includes a second half groove gland located between the inner hole and the outer hole and a second sealing member placed in the second half groove gland.
7. A device as claimed in claim 1, wherein the piston includes a first end defining a piston flange and a second end moving inside the cylinder, wherein the means for holding and moving the piston comprises an internal passageway in the actuating body having a step at its lower end above which the piston flange is mounted, a central stud mounted in the internal passageway above the piston flange, and the step and the central stud in the internal passageway defining a flange housing confining the piston flange in the actuating body, whereby holding and moving the piston while the actuating body moving in the cavity of the main body, and wherein the self adjusting means comprises a taper at the top end of the cylinder, and the piston flange having sufficient movement in the flange housing, whereby adjusting the piston position while the lower end of the piston entering the cylinder passing through the taper at the top end of the cylinder.

8. A device as claimed in claim 5, wherein the device is autoclavable and can function after going through an autoclave procedure.

9. A device as claimed in claim 1, wherein the device further includes a shield, and wherein the main body includes at least one venting hole and the shield being mounted in front of the venting hole, whereby hindering direct access of an exterior gas flow into the device for reducing the chance of contamination.

10. A device as claimed in claim 1 configured to generate negative pressure or vacuum, wherein the chamber further includes a bleeding passageway connecting chamber cavity to the exterior providing a passage for air or a gas out of the chamber cavity to the exterior of the chamber, a bleeding nut threadably mounted in the exterior end of the bleeding passageway, and vacuum sealing means to provide sealing between the bleeding nut and the bleeding passageway for sealing the bleeding passageway after passing air or the gas out of the chamber cavity to the exterior of the chamber.

11. A device as claimed in claim 1, wherein the chamber further includes a breathing passageway extending from the cylinder to the cavity of the main body providing a passage for air or a gas into the chamber cavity while the piston reciprocating in the cylinder.

12. A device as claimed in claim 1, wherein, the piston having a first end extending out of the actuating body adopted to engage to an external actuator thereof and a second end entering the cylinder to generate pressure.

13. A chamber comprising a chamber cavity wherein hydrostatic pressure is generated, the chamber configured to connect to a pressure monitoring device, the chamber further comprising a passageway extending between the chamber cavity to the exterior of the chamber, the passageway includes an outer hole and an inner hole being interconnected, the inner hole has a smaller cross-sectional area than that of the other hole, the inner hole connects the outer hole to the chamber cavity, and the pressure monitoring device threadably mounted in the outer hole, the chamber further comprising sealing means for providing a seal between the pressure monitoring device and the chamber, the sealing means defines a face seal, which includes a half groove gland located between the inner hole and the outer hole and a sealing member placed in the half groove gland.

14. A device for generating hydrostatic pressure, the device comprising:
   (a) a chamber comprising a chamber cavity wherein hydrostatic pressure is generated,
   (b) a pressure generating assembly configured to connect to the chamber for generating hydrostatic pressure in the chamber cavity, the pressure generating assembly comprising:
      (i) a main body, which includes a main body passageway extending along the length of the main body;
      (ii) a piston moving inside the chamber cavity to generate hydrostatic pressure;
      (iii) piston sealing means for providing a seal around the piston and with the interior walls of the chamber cavity;
      (iv) an actuating body threadebly moving in the main body passageway;
      (v) the actuating body comprising means to hold and move the piston;
      (vi) self adjusting means to adjust the piston position for entering inside the chamber cavity;
   (c) connecting means to connect the pressure generating assembly to the chamber.

15. A device as claimed in claim 14, wherein the chamber cavity holding materials comprising a fluid medium.

16. A device as claimed in claim 14, wherein the connecting means is configured to connect the main body of the pressure generating assembly to the chamber by a threading mechanism, a plurality of fastening bolts and nuts, or draw latches.

17. A device as claimed in claim 14, the device further comprises a pressure monitoring device wherein the chamber is configured to connect to the pressure monitoring device, and sealing means for providing a seal between the pressure monitoring device and the chamber.

18. A device as claimed in claim 17, wherein the chamber comprises a passageway extending between the chamber cavity to the exterior of the chamber, the passageway includes an outer hole and an inner hole being interconnected, the inner hole has a smaller cross-sectional area than that of the other hole, the inner hole connects the outer hole to the chamber cavity, and the pressure monitoring device threadably mounted in the outer hole, and wherein the sealing means between the pressure monitoring device and the chamber defines a face seal, which includes a half groove gland located between the inner hole and the outer hole and a sealing member placed in the half groove gland.

19. A device as claimed in claim 14, wherein the piston includes a first end defining a piston flange and a second end moving inside the chamber cavity, wherein the means for holding and moving the piston comprises an internal passageway in the actuating body having a step at its lower end above which the piston flange is mounted, a central stud mounted in the internal passageway above the piston flange, and the step and the central stud in the internal passageway defining a flange housing confining the piston flange in the actuating body, whereby holding and moving the piston while the actuating body moving in the passageway of the main body, and wherein the self adjusting means comprises a taper at the top end of the chamber cavity, and the piston flange having sufficient movement in the flange housing, whereby adjusting the piston position while the lower end of the piston entering the chamber cavity passing through the taper at the top end of the chamber cavity.

20. A device as claimed in claim 17, wherein the device is autoclavable and can function after going through an autoclave procedure.

21. A device as claimed in claim 14, wherein the device further includes a shield, and wherein the main body includes at least one venting hole and the shield being mounted in front of the venting hole, whereby hindering direct access of an exterior gas flow into the device for reducing the chance of contamination.

22. A device as claimed in claim 14, wherein the device further includes a breathing passageway extending from the chamber cavity to the exterior of the chamber providing a passage for air or a gas into the chamber cavity while the piston reciprocating in the chamber cavity.

23. A device as claimed in claim 14 configured to generate negative pressure or vacuum, wherein the chamber further includes a bleeding passageway connecting chamber cavity to the exterior providing a passage for air or a gas out of the chamber cavity to the exterior of the chamber, a bleeding nut threadably mounted in the exterior end of the bleeding passageway, and vacuum sealing means to provide sealing between the bleeding nut and the bleeding passageway for sealing the bleeding passageway after passing air or the gas out of the chamber cavity to the exterior of the chamber.

24. A device as claimed in claim 14, wherein, the piston having a first end extending out of the actuating body adopted to engage to an external actuator thereof and a second end entering the chamber cavity to generate pressure.

25. A device as claimed in claim 14 wherein the main body is integral with the chamber.

26. A device as claimed in claim 1, wherein the piston is integral with the actuating body, the piston includes a first end having an attachment to the lower end of the actuating body and a second end moving inside the cylinder of the main body, wherein the means for holding and moving the piston is provided by the attachment of the first end of the cylinder to the actuating body, and wherein the self adjusting means comprises a taper at the top end of the cylinder of the main body allowing a smooth entry of the second end of the piston into the cylinder.

27. A device as claimed in claim 14, wherein the piston is integral with the actuating body, the piston includes a first end having an attachment to the lower end of the actuating body and a second end moving inside the chamber cavity, wherein the means for holding and moving the piston is provided by the attachment of the first end of the cylinder to the actuating body, and wherein the self adjusting means comprises a taper at the top end of the chamber cavity allowing a smooth entry of the second end of the piston into the chamber cavity.

\* \* \* \* \*